United States Patent [19]

Bosone et al.

[11] 4,425,357
[45] Jan. 10, 1984

[54] ACYL ANILINES EXERTING A FUNGICIDAL ACTION

[75] Inventors: Enrico Bosone, Milan; Giovanni Camaggi, Lodi, both of Italy; Lambertus de Vries, Hilversum, Netherlands; Carlo Garavaglia, Cuggiono, Italy; Luigi Garlaschelli, Pavia, Italy; Franco Gozzo, San Donato Milanese, Italy; Jan C. Overeem, Scherpenzeel, Netherlands; Simone Lorusso, San Giuliano Milanese, Italy

[73] Assignee: Montedison S.p.A., Milan, Italy

[21] Appl. No.: 261,963

[22] Filed: May 8, 1981

Related U.S. Application Data

[62] Division of Ser. No. 8,584, Feb. 1, 1979, Pat. No. 4,291,049.

[30] Foreign Application Priority Data

Feb. 2, 1978 [IT] Italy .................. 19896 A/78
Jul. 4, 1978 [IT] Italy .................. 25295 A/78

[51] Int. Cl.³ .................. C07C 103/22; C07C 103/76; A01N 37/22
[52] U.S. Cl. .................. 424/278; 260/465 D; 549/373; 549/451; 560/16; 560/43; 560/44; 560/41; 564/154; 564/155; 564/158; 564/169; 564/200; 564/207; 564/170; 564/182; 564/184; 564/187; 424/304; 424/309; 424/324
[58] Field of Search .................. 560/41, 43, 16, 44; 564/169, 170, 182, 184, 154, 155, 158, 187, 200, 207; 424/309, 324, 304, 278; 260/265 D, 338, 465 D; 549/449

[56] References Cited

U.S. PATENT DOCUMENTS 3,904,669 9/1975 Boroschewski et al. ............ 560/41
4,021,224 5/1977 Pallos et al. ............ 560/43
4,093,738 6/1978 Hubele ............ 560/43
4,237,268 12/1980 Walz et al. ............ 560/43
4,284,791 8/1981 Leenkenheimer et al. ............ 560/43

Primary Examiner—Michael L. Shippen

[57] ABSTRACT

Acyl anilines are disclosed having the formula

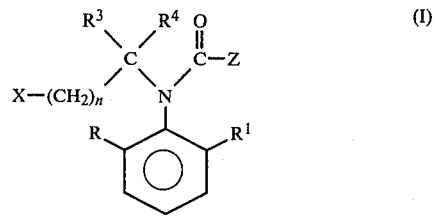

wherein
R and R¹ (like or unlike each other)=H; CH₃; C₂H₅; n.C₃H₇; —CH₂—CH=CH₂; —CH=CH—CH₃;
R³ and R⁴ (like or unlike each other)=H; alkyl C₁–C₃; halomethyl; Cl; F; CN; O-alkyl; S-alkyl; alkoxymethyl; or
R³ and R⁴ together are (CH₂=)

$$X = -\underset{\underset{O}{\|}}{C}-R^9; -\underset{\underset{O}{\|}}{C}-O-R^9 \ (R^9 = \text{alkyl } C_1\text{-}C_3); \text{CN};$$

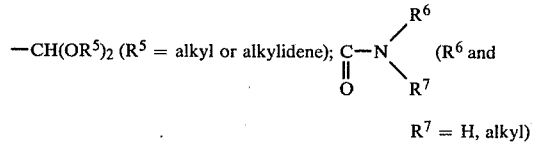

$R^7 = H$, alkyl)

n=0,1
Z=phenyl optionally substituted;

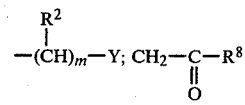

And R²=H, CH₃; m=1,2;
Y=alkynyl C₂–C₈; phenyl optionally substituted; phenyl-acetyl; furyl; thienyl; pyridyl; heterocyclic groups containing 2 or 3 heteroatoms, one of them different from nitrogen;
R⁸=CH₃; alkoxymethyl; halomethyl; O-alkyl.

The compounds of formula I are endowed with a high fungicidal activity and with a low phytotoxicity.

14 Claims, No Drawings

ACYL ANILINES EXERTING A FUNGICIDAL ACTION

This is a division of our application Ser. No. 8,584, filed Feb. 1, 1979, now U.S. Pat. No. 4,291,049 issued Sept. 22, 1981.

BACKGROUND OF THE INVENTION

The bactericidal and fungicidal activity of some derivatives of aniline and of glycine having, on the nitrogen atom, a variously substituted phenyl and an acyl group of various nature has been recently described. In particular, said acyl group may consist of an alpha or beta-haloalkanoyl (German patent application DOS No. 2,513,789, Ciba Geigy), or of an acetyl group substituted in alpha by an atom of sulphur or of oxygen bound, in its turn, to groups of various nature (French patent application No. 7,510,722, Ciba Geigy), or, furthermore, of a 2-furoyl group, a 2-thienoyl group or a pyridyl 2-carboxylic group (German patent application DOS Nos. 2,513,732 and 2,513,788, Ciba Geigy).

The microbicidal activity of methylalaninates carrying, on the nitrogen atom, a 2,6-dialkyl-phenyl and one of the following groups: cyclopropanoyl, acryloyl, crotonyl, has been described too (Swiss patent application Nos. 4,998/74, 2,906/75).

The interest in the research of new derivatives of acyl anilines having a fungicidal action derives from the necessity of finding in them a high fungicidal activity combined with the absence of phytotoxicity. In fact, some products already known, though exhibiting an excellent fungicidal action, also exhibit toxicity for the plants to be protected from the infections due to fungi.

The present invention relates to new acyl anilines and more particularly to new acyl anilines having a fungicidal action, to use and the preparation of same.

We have now found new fungicidal acyl anilines—which are an object of this invention—corresponding to the general formula:

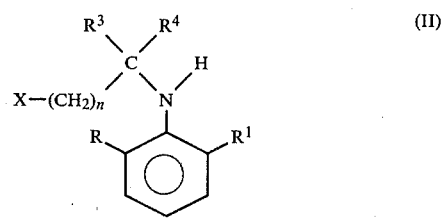

wherein
R and $R^1$ (like or unlike each other)=H; $CH_3$; $C_2H_5$; $n.C_3H_7$; $-CH_2-CH=CH_2$; $-CH=CH-CH_3$;
$R^3$ and $R^4$ (like or unlike each other)=H; alkyl $C_1-C_3$; halomethyl; Cl; F; CN; O-alkyl; S-alkyl; alkoxymethyl;
or $R^3$ and $R^4$ together are ($CH_2=$)

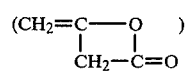

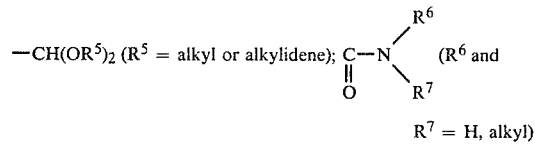

n=0,1
Z=phenyl optionally substituted;

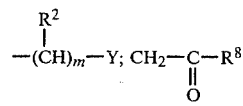

and $R^2=H$, $CH_3$; m=1,2;
Y=alkynyl $C_2-C_8$; phenyl optionally substituted; phenylacetyl; furyl, thienyl; pyridyl; heterocyclic groups containing 2 or 3 heteroatoms, one of them different from nitrogen;
$R^8=CH_3$; alkoxymethyl; halomethyl; O-alkyl.

The compounds of formula I are endowed with a high fungicidal activity and with a low phytotoxicity.

The synthesis of the acyl anilines corresponding to general formula (I) is generally carried out by condensing anilines of general formula

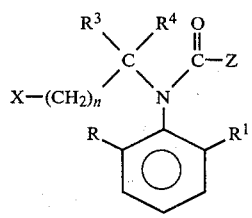

(in which $X,R,R^1$, $R^3$, $R^4$ and n have the meanings specified hereinbefore) with a compound of formula

(wherein Z has the meanings specified hereinbefore) in the presence of an halogenhydric acid-accepting base or dimethylformamide.

Some of the anilines of general formula II are available on the market, others are easily obtained by known reactions starting from 2,6-disubstituted anilines. The anilines substituted in one or both the 2 and 6 positions by alkenyl groups have been described in Italian Patent Application Nos. 23809 A/77 and 28817 A/77. As examples of compounds of general formula III can be mentioned: benzoyl chloride, phenylacetylchloride, the monochloride of a melonic ester (Cl—CO—CH$_2$—COO—alkyl), the chloride of chloro-acetoaceticacid (Cl—CO—CH$_2$—CO—CH$_2$Cl) etc.

The synthesis of compounds of formula I wherein Z=CH$_2$—CO—R$^8$ and R$^8$=CH$_3$, can also be obtained by reacting an aniline of general formula II with diketene $$(CH_2=C-O \atop | \quad | \atop CH_2-C=O)$$

The compounds reported on Table 1 have been prepared according to the methods hereinabove described.

TABLE 1

| COMPOUND | FORMULA | m.p.[a] (°C) | ELEMENTAL ANALYSIS (%) calculated C | H | N | ELEMENTAL ANALYSIS (%) found C | H | N | IR$_{max}$[b] (cm$^{-1}$) | NMR[c] (δppm) [TMS] |
|---|---|---|---|---|---|---|---|---|---|---|
| 1 | H₃C—O—C—CH(CH₃)—C(=O)—N(C(=O)—C₆H₅)—(2,6-dimethylphenyl) | 96–100 | 73.29 | 6.80 | 4.50 | 73.8 | 7.0 | 4.4 | 1635, 1730, 1745 | 1.04 (d,3H,CH₃—CH) 2.33 (s,3H,CH₃—φ) 2.29 (s,3H,CH₃—φ) 3.79 (s,3H,CH₃—O) 4.30 (q,1H,CH) 6.83–7.33 (m,8H,aromatic protons) |
| 2 | (CH₃)₂CH—O—C(=O)—CH(CH₃)—N(C(=O)—C₆H₅)—(2,6-dimethylphenyl) | 97–100 | 74.31 | 7.42 | 4.13 | 74.45 | 7.77 | 4.25 | 1630, 1715, 1720 | 1.2 (d,3H,CH₃—CH) 1.3 [d,6H,(CH₃)₂—CH] 2.3 (s,3H,CH₃—φ) 2.32 (s,3H,CH₃—φ) 4.4 (q,1H,CH₃—CH) 5.2 [m,1H,(CH₃)₂CH] 6.8–7.5 (m,8H,aromatic protons) |
| 3 | CH₃—CH—C(=O)—N(C(=O)—phenyl)—(2,6-dimethylphenyl) | 114–115 | | | | | | | | 1.20 (d,3H,CH₃—CH) 2.27 (s,3H, CH₃—φ) 2.37 (s,3H,CH₃—φ) 2.47 (s,3H,CH₃—φ) 3.83 (s,3H,CH₃—O) 4.30 (q,1H,CH₃—CH) 6.63–7.20 (m,7H, aromatic protons) |
| 4 | H₃C—O—C(=O)—CH(CH₃)—N(C(=O)—CH₂—C₆H₅)—(2,6-dimethylphenyl) | 78–80 | 78.32 | 7.12 | 4.30 | 75.34 | 7.47 | 4.67 | 1660, 1750 | 0.98 (d,3H,CH₃—CH) 1.85 (s,3H,CH₃—φ) 2.4 (s,3H,CH₃—φ) 3.25 (s,2H,CH₂) 3.8 (s,3H,CH₃—O) 4.45 (q,1H,CH₃—CH) 6.85–7.3 (m,8H, aromatic protons) |

TABLE 1-continued

| COMPOUND | FORMULA | m.p.[a] (°C.) | ELEMENTAL ANALYSIS (%) calculated | | | ELEMENTAL ANALYSIS (%) found | | | IR$_{max}$[b] (cm$^{-1}$) | NMR[c] (δppm) [TMS] |
|---|---|---|---|---|---|---|---|---|---|---|
| | | | C | H | N | C | H | N | | |
| 5 | H$_3$C—O, H$_3$C—O, CH$_3$, CH—CH$_2$, N—C(=O)—C$_6$H$_5$, 2,6-(CH$_3$)$_2$-C$_6$H$_3$ | oil | 73.37 | 7.70 | 4.18 | 75.4 | 8.4 | 4.3 | | |
| 6 | H$_3$C—O, H$_3$C—O, CH—CH$_2$, N—C(=O)—C$_6$H$_5$, 2,6-(CH$_3$)$_2$-C$_6$H$_3$ | 58-59 | 72.81 | 7.40 | 4.47 | 73.14 | 7.66 | 4.69 | | 2.2 (s,6H,CH$_3$—φ); 3.3 (s,6H,CH$_3$—O); 3.9 (d,2H,CH$_2$—N); 4.95 (t,1H, CH<O O>); 7–7.3 (m,8H, aromatic protons) |
| 7 | H$_3$C—O—C(=O)—CH(CH$_3$)—N(CH$_2$—CH=CH$_2$)—C(=O)—C$_6$H$_5$, phenyl | oil | 74.28 | 6.54 | 4.33 | 73.6 | 6.6 | 4.6 | | 1.35; 1.65 (d,d,3H,CH$_3$—CH); 3.3 (m,2H,CH$_2$—CH=CH$_2$); 3.8 (s,3H,CH$_3$—O); 4.8 (q,1H,CH$_3$—CH); 4.9; 5.15 (m,m,2H,—CH=CH$_2$); 5.6 (m,1H CH=CH$_2$); 7.1–7.35 (m,9H, aromatic protons) |
| 8 | H$_3$C—O—C(=O)—CH(CH$_3$)—N(CH$_2$-thienyl)—2,6-(CH$_3$)$_2$-C$_6$H$_3$ | 63-64 | 65.23 | 6.39 | 4.23 | 66.53 | 6.74 | 4.54 | 1665 1745 | 1.0 (d,3H, CH$_3$—CH); 2.0 (s,3H,CH$_3$—φ); 2.45 (s,3H,CH$_3$—φ); 3.4 (s,2H,CH$_2$); 3.8 (s,3H,COOCH$_3$); 4.5 (q,1H,CH$_3$—CH); 6.5–7.3 (m,6H) |

TABLE 1-continued

| COMPOUND | FORMULA | m.p.[a] (°C.) | ELEMENTAL ANALYSIS (%) | | | | | | | $IR_{max}^{[b]}$ (cm$^{-1}$) | NMR[c] (δppm) [TMS] |
|---|---|---|---|---|---|---|---|---|---|---|---|
| | | | calculated | | | found | | | | | |
| | | | C | H | N | C | H | N | | | |
| 9 | H$_3$C—O—C(=O)—CH(CH$_3$)—N(—C(=O)—C$_6$H$_4$—OCH$_3$)—C$_6$H$_3$(CH$_3$)$_2$ | 105–108 | 70.36 | 6.79 | 4.10 | 70.5 | 6.9 | 4.0 | 1630 1750 | 1.3 (d 3H, CH$_3$—CH) 2.3 (s, 6H, CH$_3$—φ) 3.7 (s, 3H, CH$_3$—O—φ) 3.85 (s, 3H, COOCH$_3$) 4.45 (q, 1H, CH$_3$—CH) 6.75–7.6(m, 7H, aromatic protons) |
| 10 | (CH$_3$)$_2$CH—O—C(=O)—CH(CH$_3$)—N(—C(=O)—CH$_2$—C$_6$H$_5$)—C$_6$H$_3$(CH$_3$)$_2$ | oil | 74.76 | 7.70 | 3.96 | 73.84 | 7.91 | 3.99 | 1650 1730 | 1.2–1.45(9H) 2.3 (s, 6H, CH$_3$—φ) 4.4 (q,1H, N—CH) 5.2 (m,—1H, COOCH) 6.8–7.5 (m, 8H, aromatic protons) |
| 11 | H$_3$C—O—C(=O)—C(=CH$_2$)—N(—C(=O)—CH$_2$—C$_6$H$_5$)—C$_6$H$_3$(CH$_3$)$_2$ | 56–57 | | | | | | | | 2.05 (s,6H,CH$_3$—φ) 3.4 (s,2H,CH$_2$—φ) 3.85 (s,3H,COOCH$_3$) 4.5–5.4 (d,d,2H,CH$_2$=C) 7.1–7.3 (m,8H, aromatic protons) |
| 12 | H$_3$C—O—C(=O)—CH(C$_2$H$_5$)—N(—C(=O)—CH$_2$—C$_6$H$_5$)—C$_6$H$_3$(CH$_3$)$_2$ | 51–52 | 74.31 | 7.42 | 4.13 | 74.03 | 7.52 | 4.07 | | |

TABLE 1-continued

| COMPOUND | FORMULA | m.p.(a) (°C.) | ELEMENTAL ANALYSIS (%) calculated | | | ELEMENTAL ANALYSIS (%) found | | | $IR_{max}^{(b)}$ $(cm^{-1})$ | $NMR^{(c)}$ ($\delta$ppm) [TMS] |
|---|---|---|---|---|---|---|---|---|---|---|
| | | | C | H | N | C | H | N | | |
| 13 | H₅C₂—O—C(CH₃)H—C(=O)—N(2,6-dimethylphenyl)—C(=O)—CH₂—C₆H₅ | oil | 74.31 | 7.42 | 4.13 | 72.96 | 7.16 | 4.34 | | |
| 14 | H₅C₂—O—C(CH₃)H—C(=O)—N(2,6-dimethylphenyl)—C(=O)—C₆H₅ | 69–70 | 73.82 | 7.12 | 4.30 | 73.41 | 7.28 | 4.31 | | |
| 15(d) | H₃C—O—C(CH₃)H—C(=O)—N(2,6-dimethylphenyl)—C(=O)—(4-Cl-C₆H₄) | 97–100 | 65.99 | 5.83 | 4.05 | 67.0 | 5.9 | 3.7 | 1630 1730 1745 | 1.27 (d,3H,CH₃—CH) 2.3 (s,6H,CH₃—φ) 3.8 (s,3H,COOCH₃) 4.45 (q,1H,CH₃—CH) 6.9–7.4 (m,7H, aromatic protons) |
| 16 | H₃C—O—C(CH₃)H—C(=O)—N(2,6-dimethylphenyl)—C(=O)—CH₂—C₆H₁₁ | 60–64 | 72.47 | 8.82 | 4.22 | 71.75 | 9.12 | 3.81 | 1650 1750 | |

TABLE 1-continued

| COMPOUND | FORMULA | m.p.[a] (°C.) | ELEMENTAL ANALYSIS (%) calculated C | H | N | found C | H | N | IR$_{max}$[b] (cm$^{-1}$) | NMR[c] (δppm) [TMS] |
|---|---|---|---|---|---|---|---|---|---|---|
| 17 | H₃C—O—C(=O)—CH(CH₃)—N(2,6-dimethylphenyl)—C(=O)—CH₂—O—C₆H₄—OCH₃ | 90–93 | 70.96 | 7.09 | 3.94 | 70.59 | 7.28 | 3.70 | 1655 1745 | |
| 18[e] | H₃C—O—C(=O)—CH(CH₃)—N(2,6-dimethylphenyl)—C(=O)—CH₂—C(=O)—CH₃ | oil | | | | | | | | 0.98 (d,3H,CH₃—CH)<br>2.12<br>2.15 (6H,CH₃—φ)<br>2.39<br>2.43<br>1.71<br>2.09 (3H,CH₃—CO)<br>2.92 (CH₂)<br>3.70 (s,3H,CH₃O)<br>4.33 (CH=C—OH)<br>4.40 (CH₃—CH)<br>6.96–7.26 (3H aromatic protons)<br>13.93 (c,OH) |
| 19[e] | H₅C₂—O—C(=O)—CH(CH₃)—N(2,6-dimethylphenyl)—C(=O)—CH₂—C(=O)—CH₃ | oil | | | | | | | | 0.99 (d,3H,CH₃—CH)<br>1.29 (t. 3H,CH₃—CH₂)<br>2.08<br>2.25 (CH₃—φ + CH₃—CO)<br>2.40<br>2.43<br>2.08–2.25 (CH₃—C=O)<br>1.71 (CH₃—C=)—OH<br>2.91 (CO—CH₂—CO)<br>4.16 (CH₂—CH₂)<br>4.37 (CH₃—CH)<br>4.30 (CH=C—OH)<br>6.93–7.24 (m,3H, aromatic protons)<br>13.90 (OH) |

TABLE 1-continued

| COMPOUND | FORMULA | m.p.[a] (°C.) | ELEMENTAL ANALYSIS (%) calculated | | | | ELEMENTAL ANALYSIS (%) found | | | | IR$_{max}$[b] (cm$^{-1}$) | NMR[c] (δppm) [TMS] |
|---|---|---|---|---|---|---|---|---|---|---|---|---|
| | | | C | H | N | | C | H | | N | | |
| 20 | [structure] | oil | 64.85 | 6.95 | 4.20 | | 64.84 | 7.24 | | 4.51 | 1660 1745 | |
| 21 | [structure] | oil | 66.83 | 7.01 | 3.90 | | 67.93 | 7.72 | | 4.67 | 1660 1745 | |
| 22 | [structure] | oil | | | | | | | | | | 0.97 (3H,d,CH$_3$—CH) 4.36 (1H,q,CH$_3$—CH) 2.87 (2H,s,CH$_2$) 3.60 3.73 } (6H,s,s,OCH$_3$) 2.20 (3H,s,CH$_3$—φ) 2.45 (3H,s,CH$_3$—φ) 7.0–7.2 (3H,m, aromatic protons) |
| 23 | [structure] | | | | | | | | | | | 0.97–0.99 (3H,d,d,CH$_3$—CH) 1.27 (3H,t,CH$_3$—CH$_2$) 2.27–2.46 (3H,s,s,CH$_3$—φ) 2.85 (2H,s,CH$_2$—CO) 2.27–3.17 (2H,m,CH$_2$—CH$_3$) 3.60–3.72 (6H,s,s,OCH$_3$) 4.37 (1H,m,CH$_3$—CH) 6.93–7.30 (3H,m, aromatic protons) |

TABLE 1-continued

| COMPOUND | FORMULA | m.p.[a] (°C.) | ELEMENTAL ANALYSIS (%) calculated C | H | N | found C | H | N | IR$_{max}$[b] (cm$^{-1}$) | NMR[c] (δppm) [TMS] |
|---|---|---|---|---|---|---|---|---|---|---|
| 24 | (structure) | | | | | | | | | 0.97 (3H,d,CH$_3$—CH)<br>1.23 (6H,t,CH$_3$—CH$_2$)<br>2.83 (2H,s,CH$_2$—CO)<br>2.13–3.17 (4H,m,CH$_2$—CH$_3$)<br>3.57–3.70 (6H,s,s,OCH$_3$)<br>4.33 (1H,m,CH—CH$_3$)<br>6.97–7.37 (3H,m, aromatic protons) |
| 25 | (structure) | 105–110 | | | | | | | | |
| 26 | (structure) | oil | 69.95 | 7.34 | 4.08 | 68.60 | 7.30 | 4.32 | 1630<br>1650<br>1720<br>1745 | |
| 27 | (structure) | oil | 68.12 | 7.30 | 4.41 | 65.85 | 7.49 | 4.35 | 1630<br>1650<br>1715<br>1745 | |

TABLE 1-continued

| COMPOUND | FORMULA | m.p.(a) (°C.) | ELEMENTAL ANALYSIS (%) calculated C | H | N | found C | H | N | IR$_{max}$(b) (cm$^{-1}$) | NMR(c) (δppm) [TMS] |
|---|---|---|---|---|---|---|---|---|---|---|
| 28 | (CH$_3$)$_2$CH—O—C(=O)—CH(CH$_3$)—N(—C(=O)—CH$_2$—C(=O)—CH$_3$)—(2,6-(CH$_3$)$_2$C$_6$H$_3$) | oil | 67.89 | 7.89 | 4.38 | 67.71 | 8.32 | 4.40 | 1630 1655 1740 | |
| 29 | H$_3$C—O—C(=O)—CH(CH$_3$)—N(—C(=O)—CH$_2$—C(=O)—CH$_3$)—(2-CH$_3$-6-CH$_2$—CH=CH$_2$-C$_6$H$_3$) | oil | 68.12 | 7.30 | 4.41 | 67.70 | 7.33 | 4.36 | 1630 1750 | |
| 30 | H$_3$C—O—C(=O)—CH(CH$_3$)—N(—C(=O)—CH$_2$—C(=O)—CH$_3$)—(2-CH$_2$—CH=CH$_2$-C$_6$H$_4$) | oil | 67.31 | 6.98 | 4.62 | 66.2 | 6.90 | 4.90 | 1630 1650 1720 1740 | |
| 31 | H$_3$C—CH$_2$—O—C(=O)—CH(CH$_3$)—N(—C(=O)—CH$_2$—C(=O)—CH$_3$)—(2,6-(CH$_3$)$_2$C$_6$H$_3$) | 84–87 | | | | | | | | |

TABLE 1-continued

| COMPOUND | FORMULA | m.p.[a] (°C.) | ELEMENTAL ANALYSIS (%) calculated C | H | N | found C | H | N | IR$_{max}$[b] (cm$^{-1}$) | NMR[c] (δppm) [TMS] |
|---|---|---|---|---|---|---|---|---|---|---|
| 32 | H₃C—O\CH—CH₂—N(C(=O)—CH₂—C(=O)—OCH₃)(2,6-dimethylphenyl) / H₃C—O | oil | 62.12 | 7.49 | 4.53 | 61.06 | 7.84 | 4.47 | 1660 1745 | |
| 33 | H₃C—O\CH₃—CH—N(C(=O)—CH₂—C(=O)—CH₃)(2,6-dimethylphenyl) / H₃C—O | oil | 66.43 | 8.20 | 4.56 | 65.76 | 8.43 | 4.89 | | |
| 34[e] | H₃C—O—C(=O)—CH₂—CH₂—N(C(=O)—CH₂—C(=O)—CH₃)(2,6-dimethylphenyl) | 65–68 | | | | | | | | 2.19 (s,3H,CH₃—φ) 2.22 (s,3H,CH₃—φ) 2.62 (t,2H,CH₂) 3.78 (t,2H,CH₂) 3.55 (s,3H,OCH₃) 2.10 (s,CH₃—CO) 1.75 (s,CH₃—C—) \| OH 2.89 (s,CH₂—CO) 4.27 (s,CH=C—) \| OH 6.93–7.20 (m,3H, aromatic protons) 14.25 (OH) |

TABLE 1-continued

| COMPOUND | FORMULA | m.p.(a) (°C.) | ELEMENTAL ANALYSIS (%) calculated C | H | N | found C | H | N | IR$_{max}$(b) (cm$^{-1}$) | NMR(c) (δppm) [TMS] |
|---|---|---|---|---|---|---|---|---|---|---|
| 35 | H₃C—O—C—CH—CH—C—CH₂—[furan]<br>∥ ∥<br>O N—O<br>H₃C—[phenyl]—CH₃ | oil | 68.55 | 6.71 | 4.44 | 67.61 | 6.70 | 4.57 | 1655<br>1740 | 1.0 (d,3H,CH₃—CH)<br>2.1 (s,3H,CH₃—φ)<br>2.4 (s,3H,CH₃—φ)<br>3.3 (s,2H,CH₂CO)<br>3.8 (s,3H,Och₃)<br>4.4 (q,1H,CH₃—CH)<br>5.9–7.5 (m,6H, aromatic protons) |

Notes to Table 1
(a)The melting points have not been corrected.
(b)Only the most meaningful bands are recorded.
(c)The NMR spectra of compounds 1 and 3 have been recorded by using CCl₄ as a solvent, the other spectra bu using CDCl₃;
 s = singlet,
 d = doublet,
 t = triplet,
 q = quadruplet,
 m = multiplet.
(d)Elemental analysis: calculated chlorine = 10.25; found chlorine = 9.68.
(e)Mixture of tautomers The compounds of general formula I are endowed with an excellent fungicidal activity towards phytopathogenous fungi, and the action exerted by same is both preventive (as it prevents the desease from arising) and curative (i.e. when the infection is already in progress).

Furthermore they possess good systemic characteristics (i.e. they are transported to the various parts of the plant) wherefore it is possible to apply them through the leaves or the soil.

The fungicidal activities of some compounds of this invention towards vine mildew [*Plasmopara viticola* (B. et C.) Berl et de Toni], tobacco mildew [*Peronospora tabacina* Adam] and tomato mildew [*Phytophthora infestans*] respectively, are recorded on tables 2, 3 and 4.

The fungicidal activity of the compounds according to the present invention has been evaluated as described in examples 14 to 22 and has been expressed in tables 2, 3 and 4 by a scale of values from 100 (total activity, sound plant) to 0 (no activity, thoroughly infected plant).

The data obtained from a comparison with Zineb, a commercial fungicide widely utilized, prove that the compounds of the present invention are by far more active, the doses being equal.

and the phytotoxicity of same. Both these data are compared with those of "Furalaxyl", a known product described in German patent application No. 2,513,788 and "Ridomil" described in German patent application No. 2,515,091. The values concerning the fungicidal activity and the phytotoxicity have been determined as described in examples 23 and 15. From the comparison between the recorded data it is clear that, with equal application doses, the compounds of this invention exhibit a fungicidal activity equal to the one of "Furalaxyl" and "Ridomil", but a by far lower phytotoxicity.

TABLE 5

| Products (see Table 1) | Curative activity against Plasmopara viticola on vine, by application to leaves effected 24 h after infection, at doses of 0.1%. | Phytotoxicity index at doses of 3%. |
| --- | --- | --- |
| 1 | 100 | 25 |
| 2 | 100 | 0 |
| 3 | 100 | 5 |
| 4 | 100 | 10 |
| *Ridomil | 100 | 100 |
| *"Furalaxyl" (check products) | 100 | 100 |

TABLE 2

Fungicidal activity against Plasmopara viticola on vine

| Compound No. | Type of action Treatment Dose (%) | Prevent. on leaves days[a] 1 | Prevent. on leaves days[a] 7 | Curative on leaves days[a] 1 | Curative on leaves days[a] 7 | Immunizing Systemic on upper leaves days[a] 1 | Immunizing Systemic on upper leaves days[a] 7 | Systemic soil days[a] 1 | Systemic soil days[a] 7 |
| --- | --- | --- | --- | --- | --- | --- | --- | --- | --- |
| 18[b] | 1 | 100 | 100 | 100 | 100 | 100 | 100 | 100 | 100 |
|  | 0.5 | 100 | 100 | 100 |  | 100 | 100 | 100 |  |
|  | 0.1 | 100 | 100 | 100 |  | 100 | 100 |  |  |
| 19[c] | 1 | 100 | 100 |  |  | 100 |  |  |  |
|  | 0.5 | 100 |  |  |  |  |  |  |  |
|  | 0.1 | 100 |  |  |  |  |  |  |  |
| Zineb (reference commercial fungicide) | 1 | 90 |  |  |  |  |  |  |  |
|  | 0.5 | 70 |  |  |  |  |  |  |  |
|  | 0.1 | 30 |  |  |  |  |  |  |  |

[a] days elasped from the treatment to the infection or vice-versa.
[b] N—(2,6-dimethylphenyl)-N—acetacetyl-α-amino-methylpropionate.
[c] N—(2,6-dimethylphenyl)-N—acetacetyl-α-amino-ethylpropionate.

TABLE 3

Fungicidal activity against Peronospora tabacina

| Compound No. | Type of action Treatment Dose (%) | Preventative on leaves days[a] 2 | Curative on leaves days[a] 2 |
| --- | --- | --- | --- |
| 18[b] | 1 | 100 | 100 |
|  | 0.5 | 100 | 100 |

TABLE 4

Fungicidal activity against Phytophthora infestans on tomato

| Compound No. | Type of action Treatment Dose (%) | Preventive on leaves days[a] 1 | Curative on leaves days[a] 1 | Systemic soil days[a] 3 |
| --- | --- | --- | --- | --- |
| 18[b] | 1 | 100 | 100 | 100 |
|  | 0.5 | 100 | 100 | 100 |
|  | 0.1 | — | — | 100 |

[a] days elapsed from the treatment to the infection or vice-versa.
[b] N-(2,6-dimethylphenyl)-N—acetacetyl-α-amino-methylpropionate.

Table 5 shows the fungicidal activity of some new acyl anilines within the scope of the present invention

*"Furalaxyl" = N—(2,6-dimethylphenyl)-N—(1'-carbomethoxyethyl)-2-furoylamide

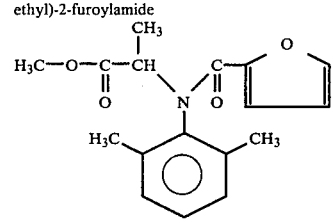

*"Ridomil" = N—(2,6-dimethylphenyl)-N—(1'-carbomethoxy-ethyl)-methoxyacetamide

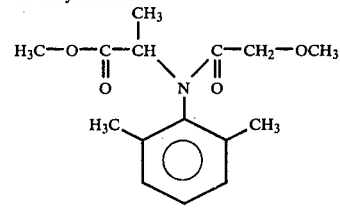

The damages caused by phytotoxicity to the plants cannot be avoided by using the dose of fungicidal product, which results to be the best compromise between the fungicidal activity of the product and its phytotoxicity. In fact in the practical application in agriculture, the fungicidal product amount which actually remains on the plant varies even remarkably in relation to weather conditions (especially frequency of precipitations), to the correctness and frequency of the treatments effected by the farmer. It is therefore necessary to have available fungicidal products endowed with a good activity as well as with a wide margin of safety, so that even high doses of product cannot damage the plants.

The following Table 6 shows a comparison between the fungicidal activity of some compounds object of the present invention and the activity of "Furaldxyl" and of "Ridomil" at different application doses, and the phytotoxicity of the same compounds at increasing doses.

From the comparison between the data recorded on Table 6 it is evident that the fungicidal activity of the compounds of this invention is of the same order of magnitude as the one of the check compounds, but the phytotoxicity is substantially lower as the application dose increases.

TABLE 6

| Compound (see Table 1) | Curative activity against Plasmopara vitivola on vine at indicated doses (%.) | | | | Phytotoxicity index at the indicated doses (%.) | | | |
|---|---|---|---|---|---|---|---|---|
| | 0.1 | 0.05 | 0.01 | 0.005 | 0.75 | 1.5 | 3 | 9 |
| 1 | 100 | 98 | 76 | 41 | | | 25 | |
| 2 | 100 | 80 | 70 | 60 | | | 0 | 0 |
| 4 | 100 | 100 | 100 | 100 | 0 | 0 | 10 | 37 |
| 8 | 100 | 100 | 100 | 100 | | | 30 | |
| Furalaxyl | 100 | 100 | 100 | 100 | 32 | 53 | 100 | 100 |
| Ridomil | 100 | 100 | 100 | 100 | 30 | 54 | 100 | 100 |

The following examples are given to better illustrate the present invention.

EXAMPLE 1

Preparation of
N-(2,6-dimethylphenyl)-N-acetoacetyl-α-amino-methylpropionate (Compound 18, Table 1)

7.06 g of just distilled diketone were added to 14.5 g of N-(2,6-dimethylphenyl)-2-amino-propionate of methyl in 25 ml of toluene. The reaction mixture was heated at reflux for 24 hours. After cooling and evaporation of the solvent, the residue was purified by chromatography on a silica gel column using chloroform as an eluent. There were obtained 20 g of the desired product in the form of oil, with a yield of 98% in respect of the theoretical yield.

The structure ascribed to said product was confirmed by NMR spectroscopy. Under the operative conditions adopted, the compound appears as a mixture of tautomers, as is evident from the signals corresponding to the various protons listed in Table 1.

EXAMPLE 2

Preparation of
N-(2,6-diallylphenyl)-N-acetoacetyl-α-aminomethylpropionate (compound 26, Table 1).

0.02 mol of methyl ester of N-(2,6-diallylphenyl)-α-amino propionic acid were dissolved in toluene (10 ml.). 0.025 mol of just distilled diketone were added to the solution and the whole was heated at reflux temperature for 24 hours. After cooling and evaporation of the solvent the residue was purified by chromatography on a silica gel column using a mixture of hexane and ethylacetate (4:1) as eluant. Thereby were obtained 3 g. of the desired product in form of oil.

EXAMPLE 3

Preparation of
N-(2-allyl-phenyl)-N-acetoacetyl-α-amino-methylpropionate (compound n. 30, Table 1).

0.02 mol of methyl ester of N-(2-allyl-phenyl)-α-amino-propionic acid were dissolved in 20 ml of benzene. To the solution 0.5 ml of pyridine and 0.25 mol of just distilled diketone were added. The reaction mixture was heated at reflux for 10 hours. After cooling it was diluted with benzene, washed with a hydrogen chloride solution (1% conc.) and with water. The organic phase was separated, anhydrified with $Na_2SO_4$ and the solvent was evaporated. The residue was purified by chromatography on a silica gel column using hexane-ethylacetate (4:1) as eluent.

Thereby were obtained 3 g of the desired product (oil).

EXAMPLE 4

Starting from the corresponding intermediates and following the procedures described in examples 1, 2 or 3, compounds 19, 27, 28, 29, 31, 33 and 34 (Table 1) were prepared.

EXAMPLE 5

Preparation of
N-(2-methyl-6-allyl-phenyl)-N-(carboxymethylacetyl)-α-amino-methylpropionate (compound 20, Table 1).

5 g (0.021 mol) of methyl ester of N-(2-methyl-6-allyl-phenyl)-α-amino propionic acid were dissolved in toluene (120 ml.).

3.5 g (0.027 mol) of malonic acid methyl ester monochloride ($ClCO—CH_2—COOCH_3$) were added under stirring, dropwise, in 15 minutes at room temperature to the solution. The reaction mixture was then stirred at room temperature for 1 hour then it was heated at reflux for 5 hours.

After cooling the solution was filtered and the solvent evaporated. The oily residue was purified by chromatography on a silica gel column using hexane-ethyl acetate (3:1) as eluent. Thereby were obtained 4.6 g of the desired product in form of a red oil.

EXAMPLE 6

Preparation of
N-(2,6-dimethyl-phenyl)-N-(2,2-dimethoxy-ethyl)-carbomethoxyacetamide (Compound 32, Table 1).

To a solution of N-(2,2-dimethoxyethyl)-2,6-dimethyl aniline (4.45 g, 0,02 mol), triethylamine (2.76 ml, 0.02 mol) in ethylether (25 ml.), malonic acid methyl ester monochloride (2.1 ml, 0.02 mol) was added dropwise in 15' at 0°−5° C. under stirring.

The reaction mixture was then stirred for 1 hour at 0° C. and 10 minutes at room temperature, then it was filtered, washed twice with 10 ml of a hydrogen chloride solution (5%), then with water till a neutral pH (3×10 ml).

The organic phase was anhydrified on anhydrous Na₂SO₄ and the solvent was evaporated. The residue (yellow oil) was purified by chromatography on a silica gel column using hexane-ethyl acetate (7:3) as eluent.

Thereby 2.1 g of the desired product (oil) were obtained.

EXAMPLE 7

Starting from the corresponding intermediates and operating as described in example 5 or 6, compounds 21, 22, 23, 24 and 25 were obtained.

EXAMPLE 8

Preparation of N-(2,6-dimethylphenyl)-N-(1-carbomethoxy-ethyl)-phenylacetamide (compound 4, Table 1).

17 g (0.11 mol) of phenylacetylchloride were added dropwise in 30 minutes and at room temperature, to a solution of N-(1-carbomethoxy-ethyl)-2,6-dimethyl-aniline(21.2 g at a purity of 95%, 0.1 mol) in toluene (150 ml) and dimethylformamide (1 ml.). The reaction mixture was stirred 1 hour at room temperature and 3 hours at reflux temperature, then it was cooled down to room temperature and washed with an aqueous solution of NaHCO₃ at 5% and successively with water. The organic phase was separated and anhydrified with anhydrous Na₂SO₄.

The solvent was evaporated and the rough product obtained was recrystallized from ligroin (75°–120° C.), so obtaining 26 g. of the desired product (white solid, m.p. 78°–80° C.).

EXAMPLE 9

By operating as described in example 8 and starting from the corresponding intermediates, the compounds 1,2,3,7,8,9,10,12,13,14,15,16,17 and 34 (Table 1) were obtained, however compounds 10,13 and 34 (oil at room temperature) were purified by chromatography on silica gel column (eluent:hexane-ethyl acetate (3:1) instead of crystallization.

EXAMPLE 10

Preparation of N-(2′,2′-dimethoxyethyl)-N-(2,6-dimethylphenyl)benzamide (compound 6, Table 1).

2.81 g (0.02 mol) of benzoyl chloride were added in drops in 20 minutes and at a temperature of 0°–5° C. to a solution of N-(2′,2′-dimethoxy-ethyl)-2,6-dimethyl aniline (4.45 g; 0.02 mol) in ethyl ether (20 ml) containing triethylamine (2.76 ml; 0.02 mol). The reaction mixture was stirred at room temperature for 15 minutes. The resulting salt was filtered and the solution was washed with 8 ml of an aqueous solution of hydrochloric acid at 5% and then with water up to neutral pH. The organic phase was anhydrified with anhydrous NaSO₄ and the solvent was evaporated, so obtaining 5.2 g of a white solid which, recrystallized from petroleum ether (25 ml) provided 4.5 g of product (purity=91% by GLC) with a yield of 65.5% (white solid, melting point=58°–59° C.).

EXAMPLE 11

By operating according to example 10 and starting from N-(1′-methyl-2′-2′-dimethoxy-ethyl)-2,6-dimethylaniline and from benzoyl chloride, N-(1′-methyl-2′,2′-dimethoxy-ethyl)-N-(2,6-dimethyl-phenyl)-benzamide (compound 5, Table 1) was prepared in the form of a clear oil.

EXAMPLE 12

Preparation of N-(methyl-methoxycarbonyl-methylene)-2,6-dimethyl aniline.

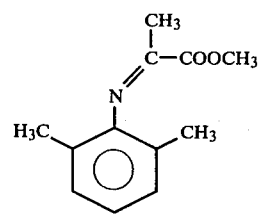

A solution of 2,6-dimethyl aniline (37.2 ml; 0.3 mol) in benzene (200 ml) was added with 0.5 g of ZnCl₂, and, dropwise at room temperature, with 33.2 ml (0.33 mol) of methyl pyruvate.

The reaction mixture was heated at reflux for 7 hours whilst azeotropically distilling the water that formed during the reaction, then the solvent was evaporated, so obtaining 65 g of an oil, which was distilled, collecting the fraction that boiled at 87°–88° C. at a pressure of 0.07 mm Hg.

42.5 g of product having a purity of 92% by GLC (yield =63.5%) were so obtained.

EXAMPLE 13

Preparation of N-(2,6-dimethylphenyl)-N-(1′-carbomethoxyvinyl)-phenylacetamide (compound 11, Table 1)

4.35 ml of phenylacetyl-chloride (0.033 mol) were added dropwise and at room temperature to a solution of 6.7 g (0.03 mol) of N-(methyl-methoxycarbonyl-methylene)-2,6-dimethyl aniline (prepared as described in example 12 and pure at 92%) in toluene (100 ml).

The reaction mixture was heated at reflux and kept in a nitrogen stream for 3 hours, whereupon the solvent was evaporated, so obtaining 10.8 g of a light yellow oil which solidified by rubbing. The rough product so obtained was crystallized from petroleum ether, obtaining 2 g of product (a white solid pure by TLC), the yield being of 21% (TLC=thin layer chromatography).

EXAMPLE 14

Preventive activity on vine mildew (*Plasmopara viticola* (B.et C.) Berl et de Toni)

Leaves of vines cv. Dolcetto, cultivated in pot in a conditioned environment at 25° C. and 60% of relative humidity, were treated by spraying onto both faces the products being tested in a hydroacetonic solution (20% by vol. of acetone). At different stretches of time from the treatment the leaves were sprayed on their lower faces with an aqueous suspension of conids of *Plasmopara viticola* (200,000 conids/cc); after a 24-hour residence time in a humidity-saturates environment, at 21° C., the plants were transferred to 70% of relative humidity and 21° C. for the incubation period (7 days). Finally, the intensity of the infection was evaluated according to indexes of an evaluation scale ranging from 100 (sound plant) to 0 (thoroughly infected plant).

EXAMPLE 15

Curative activity on vine mildew (*Plasmopara viticola* (B. et C.) Berl et de Toni)

The leaves of vine plants cv. Dolcetto, cultivated in pot in a conditioned environment at 25° C. and 60% of relative humidity, were sprayed on their lower faces with an aqueous suspension of conids of *Plasmopara viticola* (200,000 conids/cc); after a 24-hour residence time in a humidity-saturated environment at 21° C., the plants were divided into three groups. The plants of each group were treated by spraying the leaf faces with the products being tested in a hydroacetonic solution at 20% of acetone (vol./vol.), after 1, 2 and 3 days respectively from the infection.

At the conclusion of the incubation period (7 days) the seriousness of the infection was evaluated at sight according to indexes of an evaluation scale ranging from 100 (sound plant) to 0 (fully infected plant).

EXAMPLE 16

Immunizing activity on vine mildew (*Plasmopara viticola (B.et C) Berl et de Toni*)

The leaves of vine plants cv. Dolcetto, cultivated in pot in a conditioned environment, were sprayed on their upper faces with the product being tested in a hydroacetonic solution at 20% of acetone (vol./vol.).

The plants were then kept in a conditioned environment for 6 days; on the 7th day they were sprayed on their lower faces with a suspension of conids of *Plasmopara viticola* (200,000 conids/cc); after a 24-hour residence period in a humidity-saturated environment, the plants were brought again into a conditioned environment. At the conclusion of the incubation period (7 days) the seriousness of the infection was evaluated at sight according to indexes of an evaluation scale ranging from 100 (sound plant) to 0 (fully infected plant).

EXAMPLE 17

Preventive systemic activity on vine mildew

*Plasmopara viticola* (B. et C.) Berl et de Toni)

Vine plants cv. Dolcetto, cultivated in pot in a conditioned environment at 25° C. and 60% of relative humidity, were treated by introducing into the soil a hydroacetonic solution at 10% of acetone (vol./vol.) of the product being tested, at a concentration of 0.01% (referred to the earth volume).

The plants were maintained in a conditioned environment and, at different time stretches from the treatment, the leaves were sprayed on their lower faces with an aqueous suspension of conids of *Plasmopara viticola* (200,000 conids/cc). After a 24-hour residence time in a humidity-saturated environment at 21° C., the plants were transferred to 70% of relative humidity and 21° C. for the duration of the incubation period (7 days). Finally, the intensity of the infection was evaluated according to indexes of an evaluation scale ranging from 100 (sound plant) to 0 (thoroughly infected plant).

EXAMPLE 18

Preventive activity on tobacco mildew (*Peronospora tabacina* Adam)

The leaves of tobacco plants cv. Burley, cultivated in pot in a conditioned environment, were treated by spraying onto both leaf faces the product being tested in a hydroacetonic solution at 20% of acetone (vol./vol.).

2 days after said treatment the leaves were sprayed on their lower faces with an aqueous suspension of conids of *Peronospora tabacina* (200,000 conids/cc).

After a 6-hour residence period in a humidity-saturated environment, the plants were transferred to a conditioned environment at 20° C. and 70% of relative humidity for the incubation of the fungus. At the conclusion of the incubation period (6 days), the seriousness of the infection was evaluated at sight according to indexes of an evaluation scale ranging from 100 (sound plant) to 0 (fully infected plant).

EXAMPLE 19

Curative activity on tobacco mildew (*Peronospora tabacina* Adam)

The leaves of tobacco plants cv. Burley, cultivated in pot in a conditioned environment were sprayed on their lower faces with an aqueous suspension of conids of *Peronospora tabacina* (200,000 conids/cc). After a 6-hour residence in a humidity-saturated environment, the plants were divided into 2 groups and transferred into a conditioned environment at 20° C. and 70% of relative humidity for the incubation of the fungus. 24 and 48 hours after the infection the first and second group respectively were treated by spraying the product being tested in a hydroacetonic solution at 20% of acetone (vol./vol.) onto both leaf faces.

At the conclusion of the incubation period (6 days) the seriousness of the infection was evaluated at sight according to an evaluation scale ranging from 100 (sound plant) to 0 (thoroughly infected plant).

EXAMPLE 20

Preventive activity on tomato mildew (*Phytophthora infestans* (Mont) de Bary)

Leaves of tomato plants cv. Marmande, cultivated in pot in a conditioned environment at 26° C. and 60% of relative humidity, were sprayed with a hydroacetonic solution at 20% of acetone (vol./vol.) of the products being tested. After 1 day the infection was effected by spraying the lower faces of the leaves with an aqueous suspension of conids of *Phytophthora infestans* (200,000 conids/cc); after a 24-hour residence in a humidity-saturated environment at 21° C., the plants were transferred, for the incubation period (4 days), to another conditioned environment at 70% of relative humidity and at 21° C.

At the conclusion of such period, the seriousness of the infection was evaluated according to indexes of an evaluation scale ranging from 100 (sound plant) to 0 (fully infected plant).

EXAMPLE 21

Curative activity on tomato mildew (*Phytophthora infestans* (Mont) de Bary)

Leaves of tomato plants cv. Marmande, cultivated in pot in a conditioned environment at 26° C. and 60% of relative humidity, were sprayed on their lower faces with an aqueous suspension of conids of *Phytophthora infestans* (200,000 conids/cc).

After a 24-hour residence period in a humidity-saturated environment, said leaves were treated with the product being tested in a hydroacetonic solution at 20% of acetone (vol./vol.) by spraying both leaf faces. At the conclusion of the incubation period (4 days) the seriousness of the infection was evaluated at sight according to indexes of an evaluation scale ranging from 100 (sound plant) to 0 (fully infected plant).

EXAMPLE 22

Preventive systemic activity on tomato mildew (*Phytophthora infestans* (Mont) de Bary)

Tomato plants cv. Marmande, cultivated in pot in a conditioned environment at 26° C. and 60% of relative humidity, were treated by adding to the soil a hydroacetonic solution at 10% of acetone (vol./vol.) of the product being tested, at a concentration of 0.01% (referred to the earth volume).

The plants were kept in a conditioned environment and, after 3 days from the treatment, the leaves were sprayed, on their lower faces, with an aqueous suspension of conids of *Phytophthora infestans* (200,000 conids/cc).

After a 24-hour residence in a humidity-saturated environment at 21° C., the plants were transferred into another conditioned environment at 70% of relative humidity and 21° C., where they were left over the incubation period (4 days).

At the end of said period, the intensity of the infection was evaluated according to indexes of an evaluation scale ranging from 100 (sound plant) to 0 (completely infected plant).

EXAMPLE 23

Determination of the phytotoxicity

The leaves of vine plants cv. Dolcetto, cultivated in pot in a room conditioned at 25° C. and 60% of relative humidity, were treated by spraying their both faces with the products being tested in a hydroacetonic solution at 20% of acetone (vol./vol.).

The seriousness of the phytotoxic symptoms was visually evaluated after 7 days according to indexes of an evaluation scale ranging from 100 (fully damaged plant) to 0 (sound plant).

We claim:

1. A fungicidally active compound having the formula:

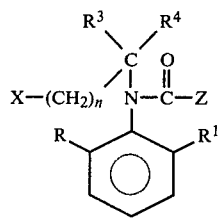

in which

R and $R^1$, the same or different, are H; $CH_3$; $C_2H_5$; n—$C_3$—$H_7$; —$CH_2$—CH=$CH_2$; —CH=CH—$CH_3$;

$R^3$ and $R^4$, the same or different, are H; $C_1$-$C_3$ alkyl; halomethyl; alkoxymethyl; Cl; F; CN; O-alkyl; S-alkyl; or together are ($CH_2$=);

X is

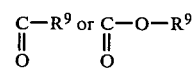

in which $R^9$ is $C_1$-$C_3$-alkyl; CN; —CH(O$R^5$)$_2$ in which $R^5$ is $C_1$-$C_3$ alkyl or alkylidene;

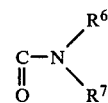

in which $R^6$ and $R^7$ are $C_1$-$C_3$ alkyl;

n is 0 or 1;

Z is

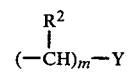

in which $R^1$ is H; $CH_3$; or

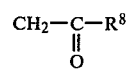

in which $R^8$ is $CH_3$, alkoxymethyl, chloromethyl or O-alkyl;

m is 1 or 2; and

Y is alkynyl $C_2$-$C_8$; phenyl; phenyl substituted by $C_1$-$C_3$ alkoxy, or phenyl acetyl.

2. A compound according to claim 1, having the formula:

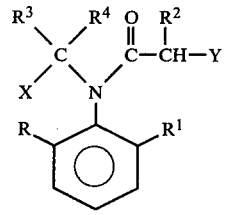

wherein R, $R^1$, $R^2$, $R^3$, $R^4$, X and Y have the same meaning as in claim 1.

3. A compound according to claim 1, having the formula:

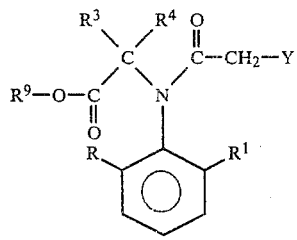

wherein R, $R^1$, $R^3$, $R^4$ and $R^9$ have the same meaning as in claim 1 and Y is phenyl or phenyl substituted by $C_1$–$C_3$ alkoxy; or phenylacetyl.

4. A compound according to claim 1 and which is N-(2,6-dimethyl-phenyl)-N-(1-carbomethoxy-ethyl)-phenylacetamide.

5. A compound according to claim 1 and which is N-(2,6-dimethyl-phenyl)-N-(1-carboisoproploxy-ethyl)-phenylac amide.

6. A compound according to claim 1 and which is N-(2,6-dimethyl-phenyl)-N-(1-carbomethoxy-vinyl)-phenylacetamide.

7. A compound according to claim 1 and which is N-(2,6-dimethyl-phenyl)-N-(1-carbomethoxy-propyl)-phenylacetamide.

8. A compound according to claim 1 and which is N-(2,6-dimethyl-phenyl)-N-(1-carbethoxy-ethyl)-phenylacetamide.

9. A compound according to claim 1 and which is N-(2,6-dimethyl-phenyl)-N-(1-carbomethoxy-ethyl)-4-methoxy-phenyl acetamide.

10. A fungicidal composition containing as active ingredient, a fungicidally effective amount of at least one of the compounds of claim 1 and an inert carrier.

11. The method for fighting infections of phythopathogenous fungi on useful plants, when the infection has not yet begun, preventive action, or when the infection is already in progress, curative action, characterized in that there is distributed on the plants or on the soil, as such or as a suitable formulation, a fungicidally effective amount of at least one compound according to claim 1.

12. The method of claim 12, in which the phytopathogenous fungi to be fought is vine mildew.

13. The method of claim 12, in which the phytopathogenous fungi to be fought is tobacco mildew.

14. The method of claim 12, in which the phytopathogenous fungi to be fought is tomato mildew.

* * * * *